(12) United States Patent
Joly et al.

(10) Patent No.: US 8,659,653 B2
(45) Date of Patent: Feb. 25, 2014

(54) DEVICE FOR EVALUATING THE SURFACE OF A TIRE

(75) Inventors: Alexandre Joly, Cournon d'Auvergne (FR); Jean-Paul Zanella, Clermont-Ferrand (FR)

(73) Assignees: Michelin Recherche et Technique S.A., Granges-Paccot (CH); Compagnie Generale des Etablissements Michelin, Clermont-Ferrand (FR)

( * ) Notice: Subject to any disclaimer, the term of this patent is extended or adjusted under 35 U.S.C. 154(b) by 596 days.

(21) Appl. No.: 12/809,595

(22) PCT Filed: Dec. 16, 2008

(86) PCT No.: PCT/EP2008/067646
§ 371 (c)(1),
(2), (4) Date: Sep. 20, 2010

(87) PCT Pub. No.: WO2009/077534
PCT Pub. Date: Jun. 25, 2009

(65) Prior Publication Data
US 2011/0018999 A1    Jan. 27, 2011

(30) Foreign Application Priority Data
Dec. 19, 2007 (FR) .................................. 07 60048

(51) Int. Cl.
*H04N 7/18* (2006.01)
*G01N 21/84* (2006.01)
*H04N 9/04* (2006.01)
*G01N 21/95* (2006.01)

(52) U.S. Cl.
USPC ............. 348/92; 348/135; 348/164; 348/136; 348/141; 348/157; 348/E5.051; 348/E7.031; 348/E5.09; 348/E9.01; 348/E7.085; 348/241; 348/228.1; 348/42; 348/87; 348/169; 348/148

(58) Field of Classification Search
USPC ....................... 348/92, 148; 356/601; 382/110
IPC ..................................... H04N 7/18; G01B 11/24
See application file for complete search history.

(56) References Cited

U.S. PATENT DOCUMENTS 6,160,902 A * 12/2000 Dickson et al. ............... 382/110
7,092,105 B2 * 8/2006 Lim et al. ...................... 356/601

(Continued)

FOREIGN PATENT DOCUMENTS

DE        199 21 650      11/2000
EP        0 547 365       6/1993

(Continued)

*Primary Examiner* — Thao Le
*Assistant Examiner* — Long Le
(74) *Attorney, Agent, or Firm* — Cozen O'Connor

(57) ABSTRACT

A device for evaluating the appearance of the surface of a tire (P) comprising a color linear camera (1) comprising means (14, 15, 16) for separating the light beam (F) reflected by the surface of said tire (P) and entering the camera (1) into at least two base colors (R, G, B) of given wavelength, so as to direct the light beam to as many sensors (11, 12, 13) capable of obtaining a basic image in gray level (41, 42, 43) for each of the base colors, as many lighting means (21, 22, 23) as base colors, said lighting means being oriented so as to light the surface to be evaluated at different angles, characterized in that each of the lighting means (21, 22, 23) emits a colored light (R, G, B) that differs from that of the other lighting means, and the wavelength of which corresponds substantially to the wavelength of one of the base colors selected by the camera.

14 Claims, 3 Drawing Sheets

(56) References Cited

U.S. PATENT DOCUMENTS

Figure 1:
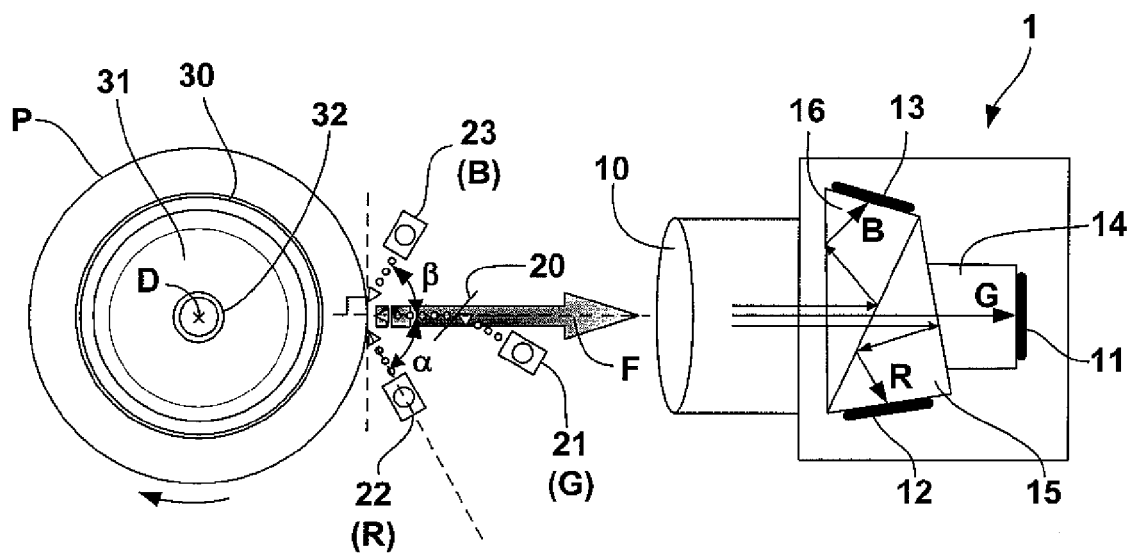

| | | |
|---|---|---|
| 7,421,108 B2 * | 9/2008 | Kaneko et al. ............... 382/141 |
| 7,768,656 B2 * | 8/2010 | Lapa et al. ................... 356/603 |
| 2005/0268707 A1 | 12/2005 | Dale et al. |
| 2010/0002244 A1 * | 1/2010 | Iino et al. .................... 356/601 |

FOREIGN PATENT DOCUMENTS

| | | |
|---|---|---|
| EP | 1 120 640 | 8/2001 |
| EP | 1 647 817 | 4/2006 |
| GB | 2 296 335 | 6/1996 |
| WO | WO 97/07380 | 2/1997 |

* cited by examiner 41
(V)

42
(R)

43
(B)

DEVICE FOR EVALUATING THE SURFACE OF A TIRE

RELATED APPLICATIONS

This is a U.S. national stage under 35 U.S.C. §371 of application No. PCT/EP2008/067646, filed on Dec. 16, 2008 and claims the priority of French application No. 07/60048, filed on Dec. 19, 2007, the entire content of which is hereby incorporated by reference.

FIELD OF THE INVENTION

The invention relates to the field of visual inspection of objects, in which it is sought to capture the image, usually digital, of a given object for the purpose, after analysis and processing, of using this image for the purposes of inspection and control. These images are designed to give information such as the color or the gray level, the texture, the brightness or the relief relative to a reference surface.

BACKGROUND OF THE INVENTION

More particularly, the invention addresses the field of acquisition of a visual image of the tires intended to be fitted to rolling vehicles. These tires usually have a black color because of the use of carbon to reinforce the elastomer mixtures on which the production of said tires is based.

Also, it is particularly awkward to interpret the images acquired with the aid of sensors sensitive to the reflection of light on the surface of the tire. The light effects generated by the relief of the tire, by grease marks, the various marks, the differences in shades of black, or by localized discolorations, can be easily confused when the raw image supplied by a camera is analyzed undiscerningly.

Various methods of image acquisition have therefore been disclosed for the purpose of supplying data as pertinent as possible to a digital processing means capable of comparing this image with a reference image in order to determine the conformity of the tire to be analyzed or to find in this image anomalies that are present on the surface of the tire.

Publication EP 1 120 640 proposes using two separate cameras that are dedicated respectively to the acquisition of the data relating to the relief and to the acquisition of the data relating to the appearance, that is to say to the data such as the color, the gray level or the brightness. The surface of the tire is lit by two sources of light each assigned to a camera. To prevent interference between the light sources it is proposed to work with different light wavelengths or to circumferentially offset the cameras and their light source.

This solution, which requires relatively bulky means, also has the disadvantage of engaging considerable computing means in order to superpose the images originating from the two acquisition means.

Publication EP 1 477 765 tries to remedy this difficulty by proposing an inspection means comprising a single camera of the matrix type associated with a slot lighting in order to carry out a single acquisition and simultaneously determine the relief and the brightness of the surface to be inspected. The determination of the brightness is based on the observation of the fact that the differences in coloration on the surface of a tire such as the grease marks have the effect of increasing or reducing the dispersion of the wavelength of the reflected image.

This acquisition method nevertheless has the drawback of being limited to the brightness analysis only, and of proposing the use of a matrix camera of which the depth of field is difficult to adjust to the curvature of the tire, and of which the resolution is inferior to that of a linear camera. Moreover, being limited to a single light source, the analysis of the zones of great relief, such as the sculptures, leaves zones of shadows that are sources of inaccuracy and the choice of the angle of observation is reduced.

To solve this problem, publication WO/2005/050131 describes two alternative solutions. According to a first alternative, it is proposed to light the surface to be analyzed with the aid of a slot light oriented substantially perpendicularly to the surface and to have two cameras oriented in two directions forming opposed angles relative to the direction of the incident light. According to a second alternative, it is proposed to capture the reflected light with the aid of two mirrors placed in two opposite directions. The light originating from these two mirrors is then recombined with the aid of a set of prisms in the direction of a single camera.

However, these solutions do not make it possible to eliminate all of the shadow zones and require the recombining of the two images, either digitally when the images originate from the two cameras, or by a fine adjustment of the minor set. Moreover, as is mentioned above, the resolution of the matrix cameras remains weak and is combined with the loss of dynamics associated with the complexity of the optical chain.

SUMMARY OF THE INVENTION

One object of the invention is to provide a solution that makes it possible to acquire the image of the surface of a tire while avoiding the effects associated with the shadow zones when the relief of the surface is very irregular, but also to provide sufficient information allowing an image-processing means to distinguish the effects of brightness associated with marks, with color variations and with effects of relief on the surface to be examined.

To do this, one embodiment of the invention uses the operating principle of color digital cameras. This type of camera contains means capable of separating into a certain number of base colors the reflected light originating from the object of which it is sought to acquire the image. As a general rule, the object is lit by a natural light or white light.

These filters may be formed by sets of prisms, or by a filter consisting of cells colored with the primary colors and better known by the name of Bayer filter. Their function is to separate the light into a certain number of colors called base colors or fundamental color. As a general rule, these filters separate the light into the three base colors or fundamental colors which are red, green and blue. However, it is also possible as an example to produce filters comprising more than three fundamental colors such as the filters capable of separating the light into four base colors comprising red, green, blue and cyan.

The reflected image originating from the object to be examined is therefore broken down into as many monochrome images as base colors or fundamental colors. Each of these images is then directed toward a specific sensor, formed by an assembly of light-sensitive photosites such as CCD or CMOS sensors capable of transforming the quantity of light that they receive into electric current. This then gives as many gray level images as base colors. The maximum resolution of a sensor is a function of the number of photosites to which the number of pixels forming the final image corresponds.

Restoring the final color image is achieved by the simultaneous combination of the monochrome images in each of the base or fundamental colors according to the known principle of additive synthesis, each of these images being able to be formed for example by the projection of the image in gray level through a filter of the corresponding base color.

An embodiment of the invention takes advantage of this operating mode in order to obtain particular information concerning the object to be evaluated.

One aspect of the invention is directed to a device for evaluating the appearance of the surface of a tire, wherein the device comprises:

a color linear camera comprising means for separating the light beam into at least two base colors of given wavelength, so as to direct the light beam to as many sensors capable of obtaining a basic image in gray level for each of the base colors, as many lighting means as base colors, said lighting means being oriented so as to light the surface to be evaluated at given angles.

This device is characterized in that each of the lighting means emits a colored light that differs from that of the other lighting means, and the wavelength of which corresponds substantially to the maximum sensitivity of the sensor of the camera designed to receive the light beam of said color.

Although it is possible, in theory, to use a matrix camera, the choice of a linear camera is preferred in the context of using the device according to the invention, for the evaluation of the surface of a tire of which the shapes are usually convex. Specifically, a linear camera makes it possible to carry out the acquisition of an image at a constant viewing angle and under a constant incidence of lighting. This type of camera also allows a better accuracy of adjustment of the depth of field and a better resolution.

In this manner, it is possible to determine the origin of the light source for each of the images in gray level of the light reflected by the object to be evaluated. In the context of an optimum adjustment, the light originating from a given base color reflected by the surface to be evaluated is filtered by the set of prisms placed at the input of the camera and directed toward the only sensor corresponding to the wavelength of this light. And the light originating from the other light sources is filtered by said set of prisms and does not reach the sensor in question.

Each of the lighting means being placed so as to light the object to be evaluated at a given angle of incidence, this amounts to obtaining simultaneously at least two different images the analysis of which will make it possible to determine the relief and the brightness of the surface of the tire. This dispenses with the need to superpose the images since they originate from the acquisition by one and the same camera of the same ray of light. And it is no longer necessary to use a set of several cameras to obtain the same result.

It will moreover be observed that the image of a tire can be produced in a single revolution, which is an additional advantage with respect to the processing times necessary for the inspection of a tire.

A calculation method associated with the evaluation device makes it possible to calculate in a known manner the coordinates of each of the pixels of the image obtained and to associate with these pixels values relating to the relief and the brightness level of the surface to be analyzed.

A first application of one embodiment of the invention uses a device in which the light beam is separated into two colors. The two images taken at different angles reveal shadow zones and different lit zones which makes it possible to deduce the nature of the relief of the surface and its orientation relative to a mean surface level.

The brightness information may be obtained, for example, by taking the mean of the brightness measured on the two images.

However, the most worthwhile application of an embodiment of the invention uses a camera capable of separating the reflected light according to the three base colors, usually corresponding to the three fundamental colors: red, green and blue, and comprising three sets of sensors assigned to each of these fundamental colors.

The user will therefore have three color lighting means respectively red, green and blue in order to light the surface of the tire to be evaluated.

According to this particular use of the invention, arrangement is then made for one of the lighting means to light the surface to be evaluated in a direction substantially perpendicular to the surface so that the image obtained on the sensor of which the color corresponds to this lighting reveals the background of the reliefs of the surface.

The other two lighting means are placed in order to reveal the reliefs and make a non-zero angle with the direction perpendicular to the surface to be examined.

The comparative analysis of the images then makes it possible to determine with accuracy the nature of the marks observed on the surface by distinguishing between the grease marks and the marks associated with markings or blemishes as will be explained in detail below.

BREIF DESCRIPTION OF THE DRAWINGS

Figure 2:
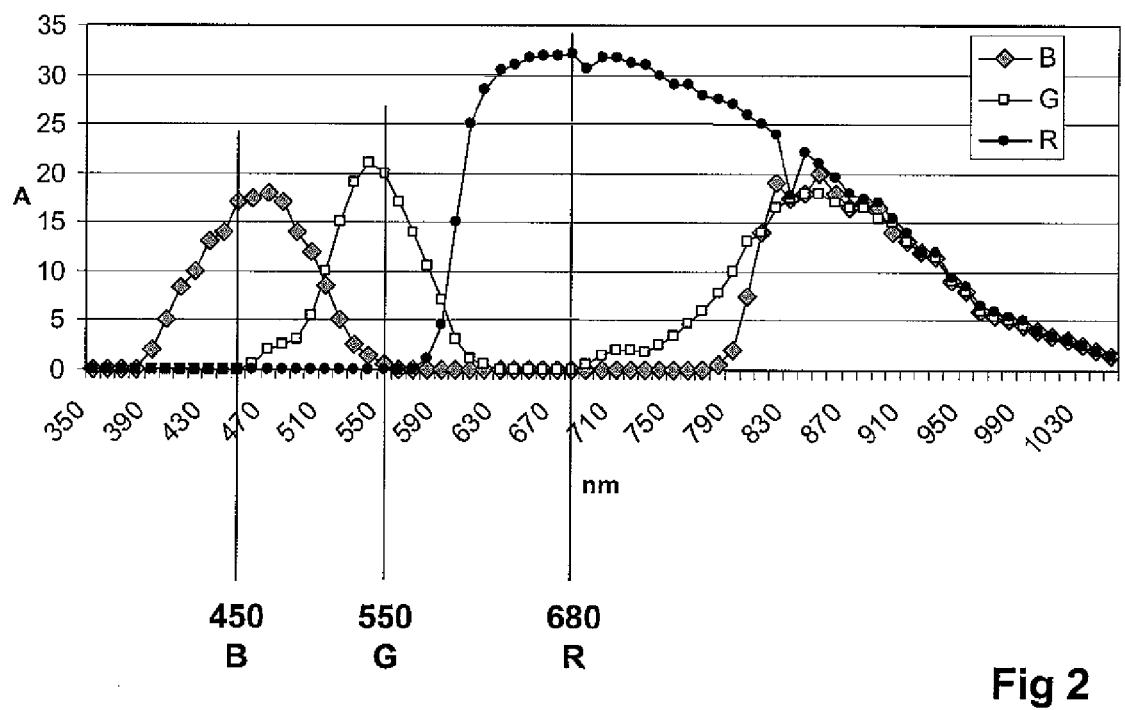
Figure 3:
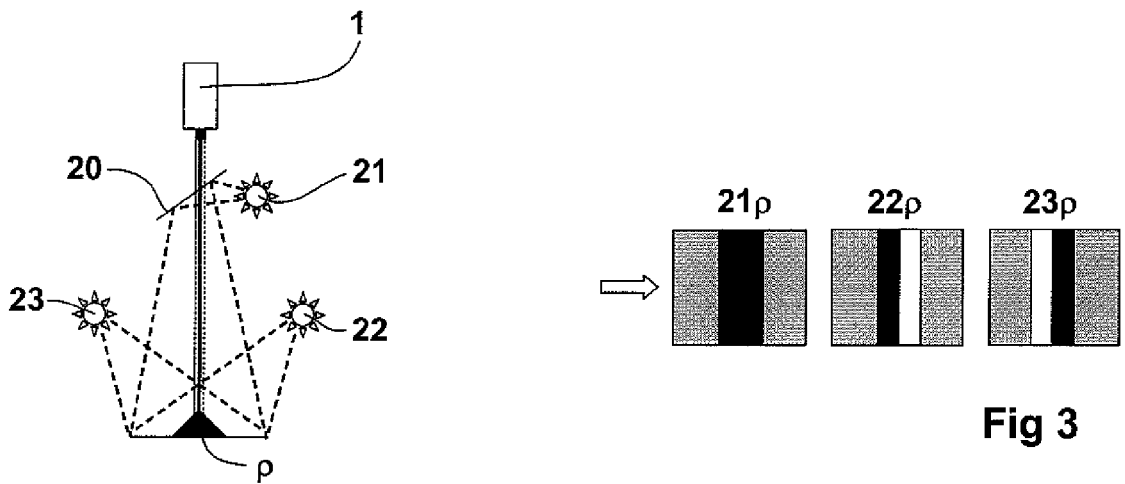
Figure 4:
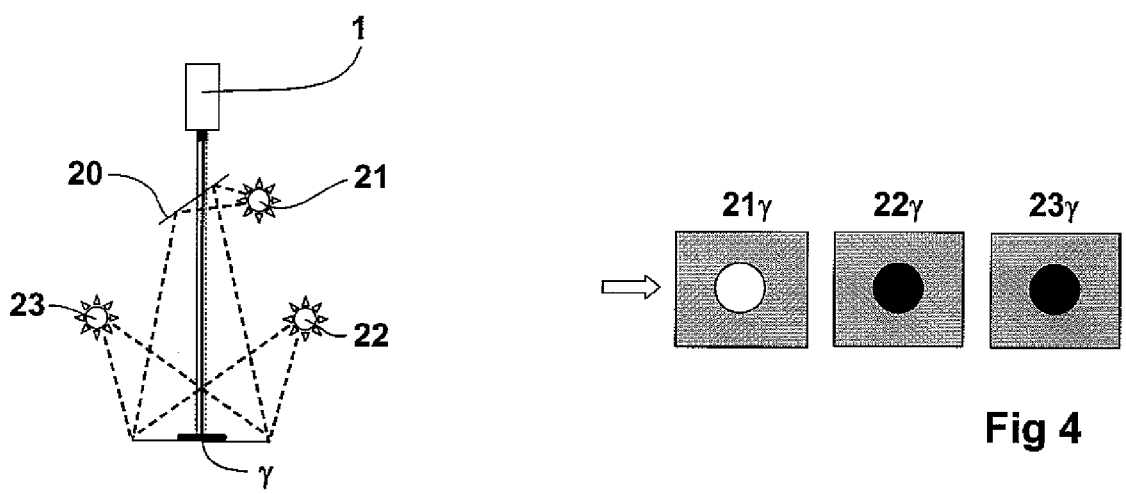
Figure 5:
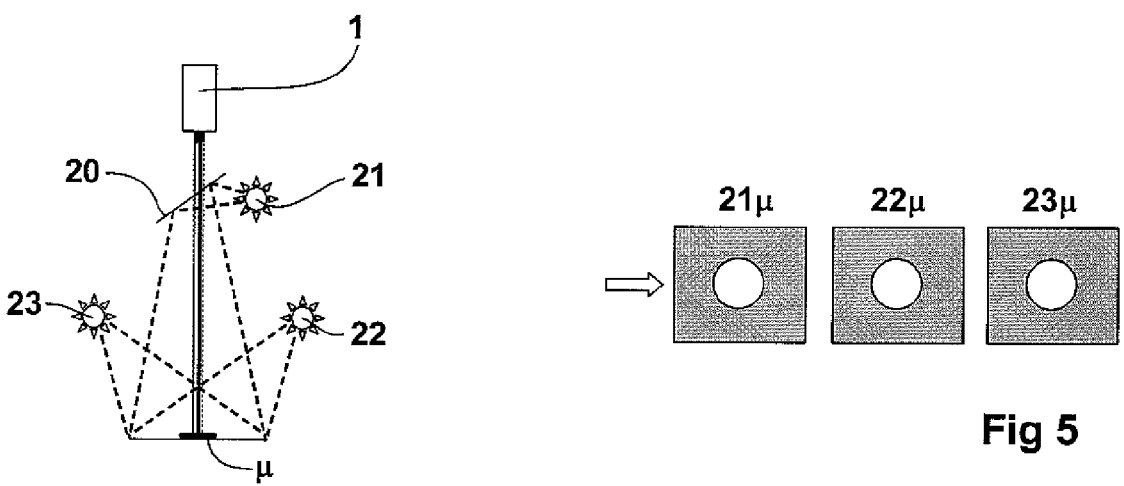
Figure 6:
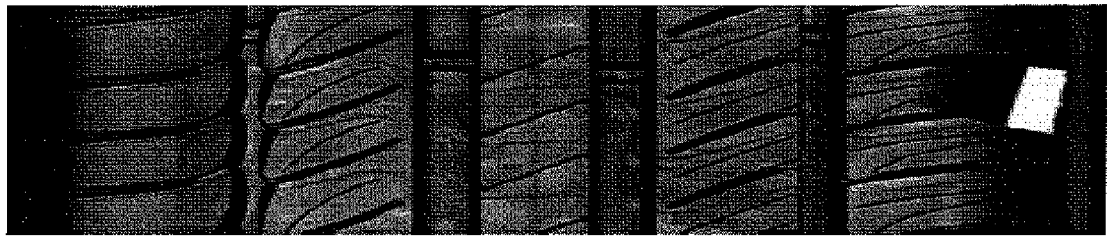
Figure 7:
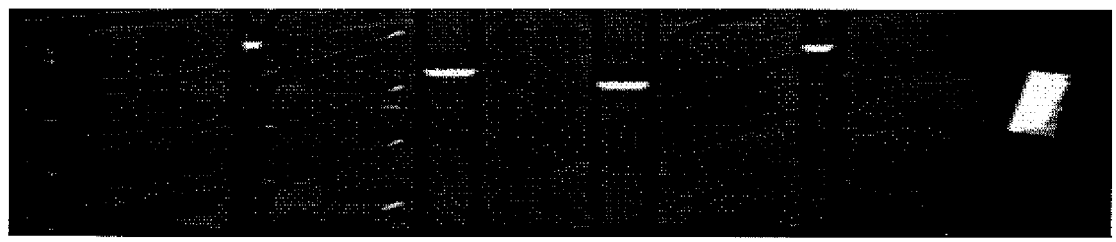
Figure 8:

FIG. 1 represents a general schematic view of a device according to an embodiment of the invention, FIG. 2 represents the sensitivity curves of the sensors of an RGB camera, FIGS. 3, 4 and 5 represent modes of analyzing the reliefs and the marks, FIGS. 6, 7 and 8 represent photographic views of the tread of a tire at different lighting angles.

DETAILED DESCRIPTION OF THE DRAWINGS

The device illustrated by FIG. 1 represents a camera 1 fitted with an input lens 10 through which the reflected light F originating from the surface of the object to be examined penetrates, in this instance the tread of a tire P. The tire P is mounted on the rim 30 of a wheel 31 rotated around the axis D by a motorized bearing hub 32.

The surface of the tire is lit by three light sources 21, 22 and 23. The light emitted by the first lighting means 21 is sent to a semireflective strip 20, placed so that the light reaches the surface to be evaluated in a direction substantially perpendicular to said surface.

Second and third lighting means are placed so as to light the surface at non-zero incident angles $\alpha$, $\beta$ relative to the direction perpendicular to the surface of the tire. In practice, it is worthwhile to obtain a grazing incidence light capable of revealing the reliefs of the surface and thus these angles $\alpha$, $\beta$ are advantageously greater than 30°.

The camera 1 is placed so as to receive the reflected rays F in a direction substantially perpendicular to the surface of reception. The light ray F penetrates the camera and lights reflecting prisms, respectively 14, 15 and 16, which will separate and reflect the light so as to orient this light toward luminosity sensors placed in the camera, respectively 11, 12 and 13, said sensors being capable of filtering the light according to a precise wavelength.

The reflecting prism 14 will allow the light of green color G to pass so that the sensor 11 forms an image in gray level of the surface corresponding only to the reflected light of green color. Arrangements are made for the color of the light emitted by the first lighting means 21 to correspond to the maximum sensitivity of this sensor 11 as illustrated in FIG. 2, in which the maximum sensitivity A of the camera for the color green G is situated as an example at around a wavelength of 550 nm for which the response of the camera is also minimal for the other two colors red and blue.

Therefore the image formed by the light sensor 11 corresponds substantially to the image of the surface lit by a light forming a right angle with the surface. This image 41, illustrated as an example in FIG. 6, makes it possible to see with accuracy the bottoms of sculpture.

The reflecting prism 15 will allow the light of color red R to pass through so that the sensor 12 forms an image in gray level of the surface corresponding only to the reflected light of color red R. The color of the light emitted by the second lighting means 22 corresponds to the maximum sensitivity of the camera for the color red, around 690 nm, and which corresponds as an example to the minimal sensitivity of the camera for the colors green and blue.

Therefore, the image in gray level formed by the sensor 12 corresponds to the image of the surface lit by a light forming an angle a with the direction perpendicular to said surface. This image 42, illustrated as an example in FIG. 7, highlights the reliefs of the sculpture of the tire by bringing out the lit zones and the shadow zones when the surface is lit by the second lighting means 22.

Finally, the reflecting prism 16 will allow the light of color blue B to pass so that the sensor 13 forms an image in gray level corresponding only to the reflected light of color blue B. The color of the light emitted by the third lighting means 23 corresponds to the maximum sensitivity of the camera for the color blue, that is 450 nm, and which corresponds as an example to the minimal sensitivity of the camera for the colors green and red.

The latter image 43, illustrated as an example in FIG. 8, highlights the shadow zones and the zones lit by the third lighting means 23.

So as to limit the spurious effects associated with the wavelengths corresponding to the near infrared, it is advantageous to place a filter on the lens of the camera that is capable of limiting the entrance of light rays with a wavelength of more than 750 nm. Other pass-band filters may also be added so as to prevent the entrance of lights of spurious wavelengths. Also, more generally, it should be sought to filter the passage of the light rays of which the wavelength is different from those used by the chosen lighting means.

This then gives three images in gray level of which the analysis will make it possible to determine the characteristics of relief and brightness of the surface to be examined. It will be observed that recombining these three images on a screen for displaying a conventional color image does not give the color image of the surface of the tire. Specifically, the light source is not a white light and each of the components of this light originates from a source having its own orientation.

The evaluation device according to the invention also comprises an analysis means capable of calculating the coordinates of each of the pixels forming the image. It will again be observed that there is no need to make adjustments for the three images previously obtained to correspond since they originate from the same light ray reflected by the surface to be examined and they are acquired by the same camera.

A first analysis consists in merging the various images in gray level, for example by taking the mean of the three values of brightness obtained at a given point. The image in gray level which results therefrom has the advantage of reducing the spurious brightness values associated with the curvature of the surface. This simple operation makes it possible to obtain a black and white image with a low noise level.

The merging of these images, by the use of a simple statistical function, also makes it possible to eliminate the impact associated with the curvature of the tire and to obtain more homogeneous acquisitions.

A second analysis makes it possible to distinguish the elements in relief by interpretation of the zones of shadow and of light at a point with given coordinates. The use of algorithms of the "shadow carving" type, of which the principle known per se consists in placing in relation the length of the projected shadow and the angle of the incident light, makes it possible to obtain an estimation of the orientation and of the size of the element in relief relative to the mean surface.

FIG. 3 makes it possible to illustrate this second type of analysis. The light reflected by the lighting means 21 is weak. The image 21ρ of the relief element ρ originating from the sensor 11 is a dark image. The image 22ρ of this same relief ρ originating from the sensor 12 will be bright on the side of the relief lit by the lighting means 22 and dark on the other side. Finally, the image 23ρ originating from the sensor 13 will be bright on the side of the relief lit by the lighting means 23 and dark on the other side. It is easy to deduce therefrom the height and the shape of the relief by a triangulation calculation.

A third comparative analysis of the images obtained by the device also makes it possible to distinguish the nature of the marks present on the surface of the tire to be evaluated.

Specifically it is known that the light reflected by a mark of a greasy nature varies considerably depending on the angle of incidence of the light source and can be likened to the reflecting effect of a mirror. This value is usually maximal when the angle of incidence is substantially equivalent to the viewing angle and reduces gradually as the difference between these angles increases. The reflection of the light is then almost total and diffusion is very limited. Also, by placing the viewing axis of the camera in a direction perpendicular to the surface, the intensity reflected by a grease mark will be maximal in this same perpendicular direction.

FIG. 4 illustrates this phenomenon. Therefore, the image 21γ originating from the sensor 11 of a mark γ of a greasy nature lit in a direction perpendicular to the surface of the mark will be bright. On the other hand, the images 22γ and 23γ of this same mark γ originating from the sensors 12 and 13 will be dark.

This phenomenon makes it possible to distinguish a greasy mark γ from a mark μ, for example a mark originating from a chalk or from a color marking means designed to identify the tire. Specifically, the image of this mark μ is not very sensitive to the variation of the angle of incidence of the lighting means. Therefore this mark μ will be seen with the same level of brightness, 21μ, 22μ and 23μ by the three sensors 11, 12 and 13, as illustrated by FIG. 5. Unlike the greasy mark, the diffusion of the light is then much greater than the reflection.

The exemplary embodiment of the invention according to the above description corresponds to the use of a standard camera comprising means for separating the light into the three fundamental colors red, green and blue.

It may however be worthwhile to use cameras having a larger number of base colors so as to increase the number of images originating from more numerous lighting means. By using a camera of the RGBE type, it is possible to have the three grazing incidence light sources in directions making an angle of 120° between them so that the relief elements can be seen more circumferentially.

Therefore, the example that has been used to support the present description is not limiting of the application of the invention the principles of which can be generalized to a larger number of lighting means and to a variety of objects of which it is sought to evaluate the geometry and the appearance and having a rough surface relief and a uniform color close to black not very well suited to revealing the shadow zones associated with the relief.

The invention claimed is:

1. A device for evaluating an appearance of a surface of a tire comprising:
    a color linear camera comprising means for separating a light beam, reflected by the surface of said tire and entering the color linear camera, into at least two different base colors of given wavelengths, so as to direct the reflected light beam to as many sensors as the at least two base colors, wherein said sensors are respectively configured to provide a basic image in gray level for each of the at least two base colors;
    a plurality of lighting means corresponding in number to said at least two base colors, each of said plurality of lighting means having its light oriented at an incident angle to the surface to be evaluated that is different from an incident angle of all other of the plurality of lighting means, and each said lighting means emitting a monochromatic light that differs in color from that of the other lighting means, wherein a wavelength of such color corresponds substantially to a maximum sensitivity of the sensor of the color linear camera configured to receive light of said color from the reflected light beam; and
    calculating means using a triangulation algorithm for calculating, from data of at least one basic image in gray level originating from a particular one of said sensors and a value of an incident angle formed by the lighting means emitting the light having the wavelength corresponding to the maximum sensitivity of the particular sensor, coordinates of pixels corresponding to relief elements in said surface.

2. The device as claimed in claim 1, further comprising means for setting in relative motion the surface of the tire relative to the color linear camera and to the lighting means.

3. The device as claimed in claim 1, wherein said calculating means associates each of said pixels with an item of information relating to a level of light intensity of the surface to be analyzed.

4. The device as claimed in claim 1, wherein the algorithm utilized by the calculating means is in accordance with "shadow carving".

5. The device as claimed in claim 4, wherein the color linear camera is configured to separate three base colors.

6. The device as claimed in claim 5, wherein the three base colors are red, green and blue.

7. The device as claimed in claim 5, wherein light beams of a second lighting means and light beams of a third lighting means are oriented in directions forming a non-zero incident angle.

8. The device as claimed in claim 6, wherein the incident angle formed by a light beam of the second and third lighting means with a vertical direction is greater than 30°.

9. The device as claimed in claim 8, wherein a lens of the camera comprises an input filter configured to block passage of light rays having a wavelength different from those utilized by a selected lighting means.

10. The device as claimed in claim 8, wherein a lens of the camera comprises an input filter configured to block passage of light rays having a wavelength greater than approximately 750 nm.

11. A method for evaluating the surface of a tire in which a device as claimed in claim 4 is used, wherein the coordinates of relief elements in the surface to be evaluated are determined by analyzing separately each said basic image in gray level originating from each of the sensors corresponding to the image of the surface seen from each lighting incident angle of each of the plurality of lighting means.

12. The method as claimed in claim 11, wherein each image in gray level formed by sensors having a wavelength which corresponds to the lighting means of light beams forming a non-zero incident angle with a direction perpendicular to the surface to be analyzed is utilized to determine coordinates of the relief elements.

13. The method as claimed in claim 11, wherein a brightness value of the surface to be evaluated is obtained by producing, at a point of an image with given coordinates, a mean of brightness values obtained on each of the images at a point with the same coordinates.

14. The method as claimed in claim 10, wherein a greasy mark is distinguished when said greasy mark is visible only on a base image originating from a sensor sensitive to light originating from whichever one of the plurality of lighting means has an incident angle substantially perpendicular to the surface.

* * * * *